United States Patent
Tverskoy

(10) Patent No.: US 9,207,690 B2
(45) Date of Patent: Dec. 8, 2015

(54) THERMAL CYCLING

(75) Inventor: Mark Tverskoy, Andover, MA (US)

(73) Assignee: Analogic Corporation, Peabody, MA (US)

( * ) Notice: Subject to any disclaimer, the term of this patent is extended or adjusted under 35 U.S.C. 154(b) by 302 days.

(21) Appl. No.: 13/241,657

(22) Filed: Sep. 23, 2011

(65) Prior Publication Data

US 2013/0078609 A1    Mar. 28, 2013

(51) Int. Cl.
*C12P 19/34* (2006.01)
*G05D 23/22* (2006.01)

(52) U.S. Cl.
CPC ............ *G05D 23/2217* (2013.01); *C12P 19/34* (2013.01)

(58) Field of Classification Search
CPC ...................................................... C12P 19/34
USPC ........................................................ 435/91.2
See application file for complete search history.

(56) References Cited

U.S. PATENT DOCUMENTS

| 5,080,165 A * | 1/1992 | Engelhardt ................ 165/46 |
| 7,010,450 B2 * | 3/2006 | Law et al. ................... 702/108 |
| 8,486,636 B2 * | 7/2013 | Enzelberger et al. ........ 435/6.12 |
| 2007/0026421 A1 * | 2/2007 | Sundberg et al. ............ 435/6 |

OTHER PUBLICATIONS

Nelson et al. (2007) Sensors and Actuators A 140 pp. 51-59.*

* cited by examiner

*Primary Examiner* — Ardin Marschel
(74) *Attorney, Agent, or Firm* — Anthony M. Del Zoppo, III; Driggs, Hogg, Daugherty & Del Zoppo Co., LPA

(57) ABSTRACT

A processing apparatus includes a carrier receiving region configured to receive a sample carrier with at least one channel that carries at least one sample. The apparatus further includes a thermal control device configured to thermal cycle the sample carrier when the sample carrier is installed in the carrier receiving region, thereby thermal cycling the sample carried therein. The apparatus further includes a thermal control system configured to control the temperature control device based on a predetermined set of target sample temperatures and a temperature map, which maps the predetermined set of target sample temperatures to a set of temperatures of the temperature control device. The set of temperatures of the temperature control device is different from the predetermined set of target sample temperatures, and the set of temperatures of the temperature control device thermal cycle the sample carrier with the temperatures of the predetermined set of target sample temperatures.

22 Claims, 6 Drawing Sheets

THERMAL CYCLING

TECHNICAL FIELD

The following generally relates to thermal cycling and is described with particular application to DNA sample processing such as DNA sequencing; however, the following is also amenable to other DNA sample processing and/or non-DNA sample processing.

BACKGROUND

A micro-channel device, such as a biochip, a lab-on-a-chip, etc. has been used to carry a small volume of a sample such as a DNA sample in one or more channels for processing, which, in one instance, has included thermal cycling the sample. By way of example, DNA sequencing has included replicating DNA fragments by a process called polymerase chain reaction (PCR), which requires rapid and precise thermal cycling of the sample multiple times through a predetermined set of temperatures. Unfortunately, temperature fluctuations from any of the predetermined temperatures of more than a half a degree may degrade replication.

A thermoelectric cooler (TEC), such as a Peltier device, is a thermoelectric heat pump, which transfers heat from one side of the device to the other side of the device, and has been used in connection with DNA sequencing for thermocycling samples. In use, a voltage is applied across the TEC device, which is in thermal communication with the portion of the micro-channel device carrying the DNA fragment for PCR, to create a temperature gradient for transferring heat away from the sample to cool the sample and towards the sample to heat the sample to thermal cycle the sample. The polarity of the applied voltage determines whether the device heats or cools the sample.

For PCR, the temperature of a fragment has been estimated based on a temperature at the periphery of the micro-channel device. This temperature is used to regulate the temperature of the TEC device to thermal cycle the DNA fragment based on the set of predetermined temperatures. Unfortunately, this temperature does not well-reflect the temperature of the sample channels. For example, FIG. 1 shows a temperature 102 at the periphery of the device and temperatures 104, 106, 108 at different channels of the device for three different target temperatures 110, 112, 114. As shown, the temperatures 104-108 do not track well to the temperature 102. As a consequence, replication may be degraded.

SUMMARY

Aspects of the application address the above matters, and others.

In one non-limiting aspect, a sample processing apparatus includes a carrier receiving region configured to receive a sample carrier with at least one channel that carries at least one sample. The apparatus further includes a thermal control device configured to thermal cycle the sample carrier when the sample carrier is installed in the carrier receiving region, thereby thermal cycling the sample carried therein. The apparatus further includes a thermal control system configured to control the temperature control device based on a predetermined set of target sample temperatures and a temperature map, which maps the predetermined set of target sample temperatures to a set of temperatures of the temperature control device. The set of temperatures of the temperature control device is different from the predetermined set of target sample temperatures, and the set of temperatures of the temperature control device thermal cycle the sample carrier with the temperatures of the predetermined set of target sample temperatures.

In another non-limiting aspect, a method includes controlling a temperature of a thermal control device, which is in thermal communication with a channel of a sample carrier carrying a sample being processed, based on a set of target sample temperatures and a temperature map, which maps the set of target sample temperatures to a set of temperatures of the thermal control device that thermal cycle the sample based on the set of target sample temperatures.

In yet another non-limiting aspect, a method for determining a temperature map that maps a set of target temperatures of a sample to a set of temperatures of a thermal control device used to thermal cycle a channel carrying the sample at the set of target temperatures, includes obtaining the set of target temperatures of the sample. The method further includes controlling a temperature of the thermal control device so that a temperature of a channel of a calibration carrier is at the set of target temperature. The method further includes measuring the temperature at a periphery of the calibration carrier concurrently with controlling the temperature of the thermal control device so that the temperature of the channel is at the set of target temperatures. The method further includes determining the temperature map based on the temperature of the channel and the temperature at the periphery of the calibration carrier.

In yet another non-limiting aspect, a calibration carrier includes a plurality of channels and one or more thermocouples, each thermocouple affixed to a different channel of the plurality of channels. The one or more thermocouples are configured to generate a signal that maps temperatures at one or more of the plurality of channels to temperatures applied to the calibration carrier.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
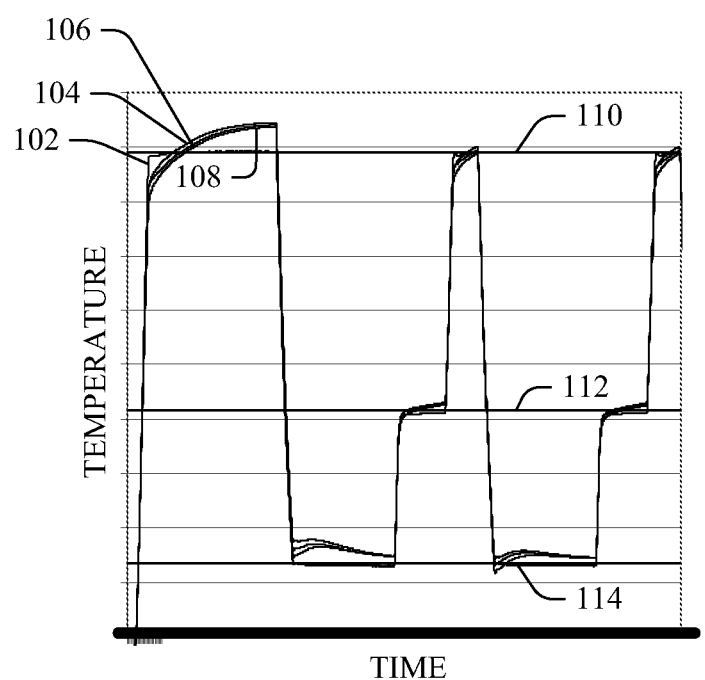
FIG. 1 illustrates an example graph showing the temperature at the periphery of a micro-channel device and channel temperatures for a set of predetermined target temperatures using a prior art approach to thermal cycle the sample at the set of predetermined target temperatures.
Figure 2:
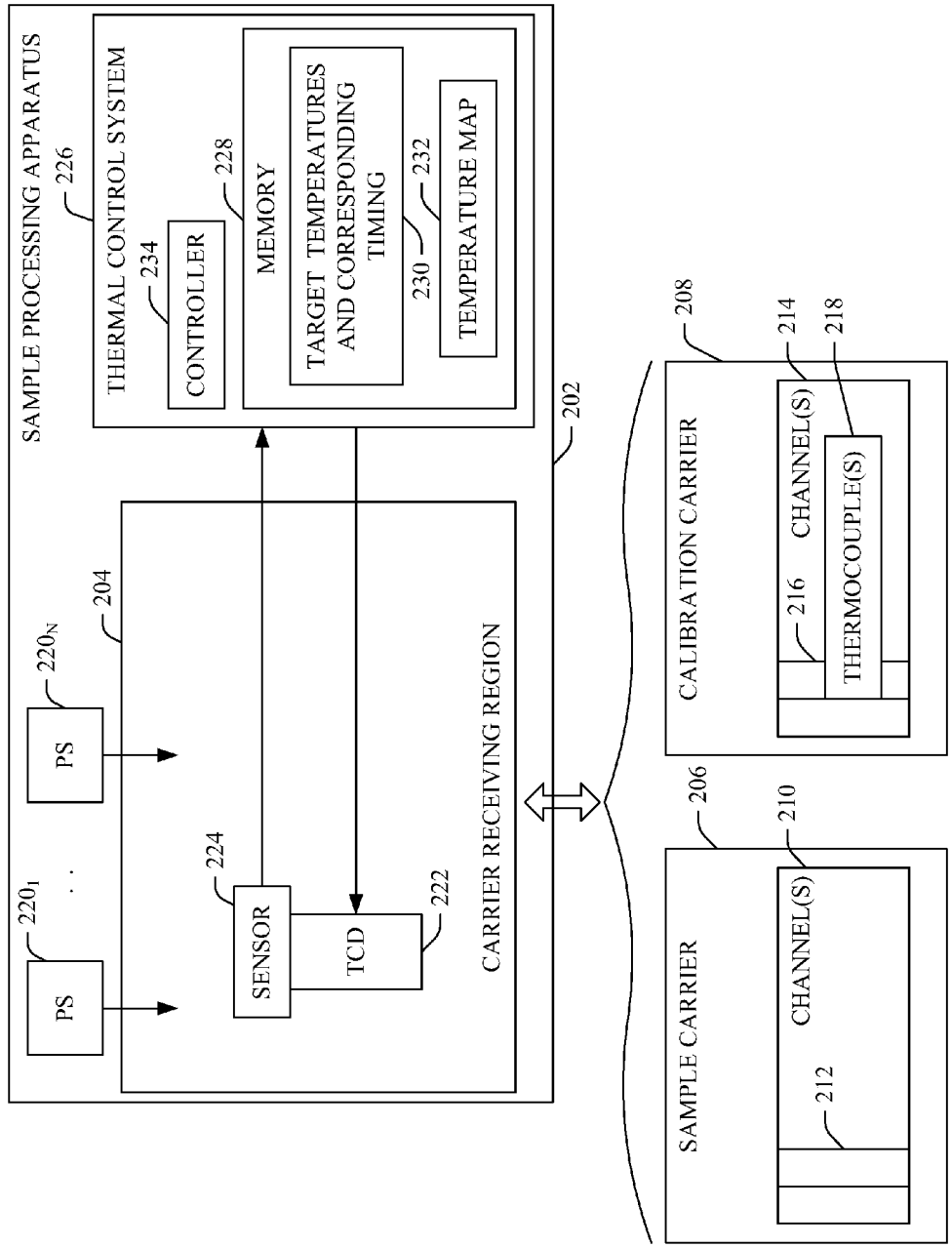
FIG. 2 illustrates an example sample processing apparatus, including a thermal control system for controlling thermal cycling a thermal control device used to thermal cycle samples.

FIG. 2 illustrates a portion of a sample processing apparatus 202, which is configured to concurrently process multiple samples, for example, DNA samples in connection with DNA sequencing. In other embodiment, the sample processing apparatus 202 is configured to process other samples, individually or in parallel, for example, in connection with enzymatic, protein, and/or other analysis.

Figure 3:
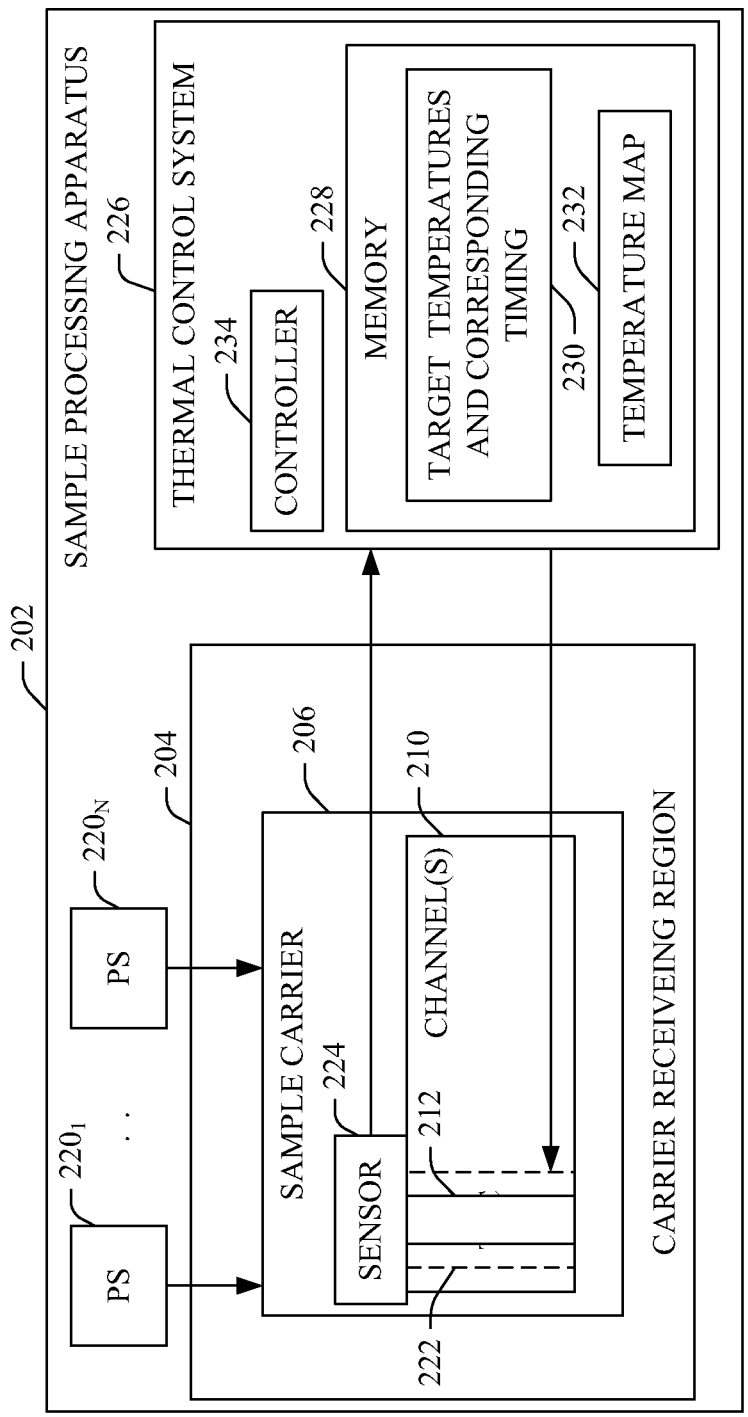
FIG. 3 illustrates the sample processing apparatus of FIG. 2 with a sample carrier installed therein.
Figure 4:
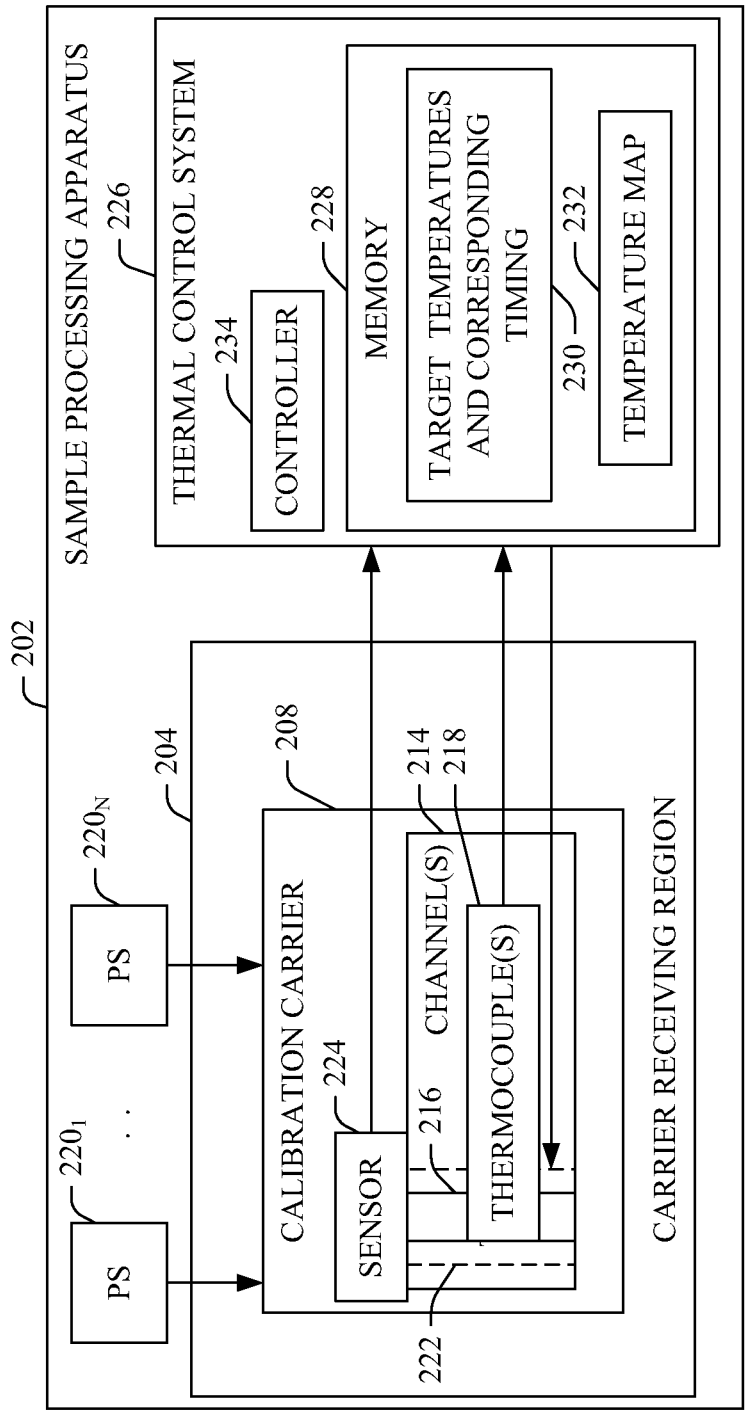
FIG. 4 illustrates the sample processing apparatus of FIG. 2 with a calibration carrier installed therein.

The sample processing apparatus 202 includes a carrier receiving region 204, which is configured to receive a carrier such as a sample carrier 206 or a calibration carrier 208. FIG. 3 shows the sample processing apparatus 202 with the sample carrier 206 installed therein, and FIG. 4 shows the sample processing apparatus 202 with the calibration carrier 208 installed therein. The carrier receiving region 204 supports the carrier installed in the sample processing apparatus 202.

The sample carrier 206 includes a micro-channel device such as a biochip, a lab-on-a-chip, etc. with one or more micro-channels 210, each configured to carry a bio-sample such as a DNA sample, blood, saliva, skin cells, etc. for processing. The sample carrier 206 also includes at least a PCR region 212.

The calibration carrier 208 is similar to sample carrier 206 in that the calibration carrier 208 is made out of a material with similar thermal properties, has similar geometry, includes a plurality of micro-channels 214, and has a PCR region 216. However, the calibration carrier 208 also includes a plurality of thermocouples 218, each in thermal communication with a different one of the micro-channels 214 in the PCR region 216. In one instance, each channel includes its own thermocouple. In another instance, only a sub-set (e.g., first, middle and last, or other combination) of the channels include thermocouples. The thermocouples 218 generate signals indicative of the temperatures of the channels 214 in the PCR region 216.

The processing apparatus 202 further includes one or more processing stations (PS) $220_1, \ldots, 220_N$ (wherein N is an integer equal to or greater than one), which are configured to process the samples carried by the sample carrier 206. In the context of DNA processing, the processing stations 220 are configured to carry out acts such as extraction/purification of DNA fragments from a sample, labeling of the extracted fragments with different fluorescent dyes, replication of the labeled fragments, separation of the replicated labeled fragments, and analysis of the separated fragments.

In the illustrated embodiment, replication, generally, is achieved through polymerase chain reaction (PCR), which includes thermal cycling, one or more times (e.g., 10-50), the DNA fragments rapidly and precisely over a set of temperatures respectively corresponding to denaturing, annealing and extending, while maintaining each temperature for a predetermined duration of time. In one instance, the set of temperatures includes: 94±0.25° C. for denaturing, 56±0.25° C. for annealing and 70±0.25° C. for extending. In another instance, one or more of the temperatures and/or tolerances may be different.

A temperature control device 222 (TCD) such as a thermoelectric cooler (TEC) (e.g., a Peltier device or the like) or other temperature control device, is configured to thermal cycle at least a portion of a loaded carrier. As shown in FIG. 3, when the sample carrier 206 is loaded in the carrier receiving region 204, the TCD 222 is in substantial thermal contact with the PCR region 212. As shown in FIG. 4, when the calibration carrier 208 is loaded in the carrier receiving region 204, the TCD 222 is in substantial thermal contact with the PCR region 216.

A temperature sensor 224 is configured to measure a temperature at the periphery of sample carrier 206 next to the PCR regions 212 and 216. The sensor 224 generates a signal indicative of the measured temperature.

A thermal control system 226 includes computer readable storage medium such as physical memory 228 in which a predetermined set of target sample temperatures and corresponding timing 230 (e.g., temperatures and timing for PCR) for a loaded carrier are stored. The memory 228 also includes a temperature map 232, which includes values that map the predetermined set of target sample temperatures of the target temperatures and corresponding timing 230 to a set of temperatures at of the TCD 222 which regulates the temperature of the channels 210 in the PCR region 212 and hence the samples therein at the predetermined set of target sample temperatures.

The thermal control system 226 also includes a processor 234 that controls the TCD 222. Where the TCD 222 includes a Peltier device, this includes applying a voltage across the TCD 222 to regulate the temperature of the TCD 222 and hence the portion of the loaded carrier in substantial thermal contact with the TCD 222, which, in this example includes the PCR region 212 of the sample carrier 206 or the PCR region 216 of the calibration carrier 208. The illustrated thermal control system 226 is configured to operate in at least two modes of operation, including a calibration mode in which data for generating the temperature map 232 is obtained and a sample processing mode in which a sample carried by the sample carrier 206 is processed using the temperature map 232.

Figure 5:
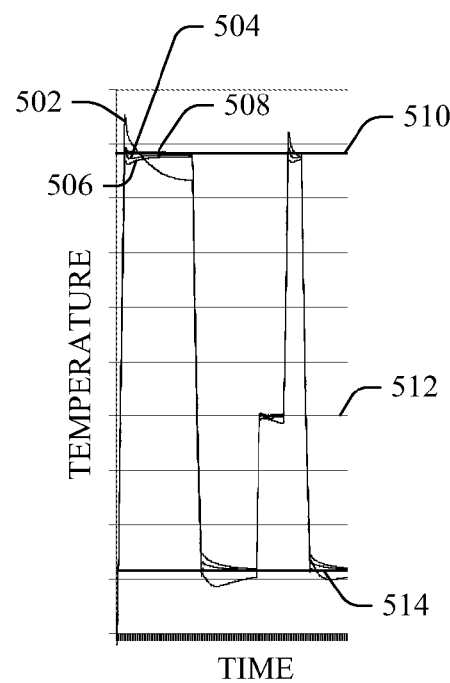
FIG. 5 illustrates an example graph showing the relationship between thermal control device temperatures and sample carrier channel temperatures, which are maintained at the set of predetermined sample target temperatures.

In calibration mode, the thermal control system 224 controls the temperature of the TCD 222 and hence the temperature of the channels 214 in the PCR region 216 based on the predetermined set of target temperatures and the temperatures of the channels 214 in the PCR region 216, which are measured by the thermocouples 218. FIG. 5 illustrates an example graph showing the relationship between temperatures 502 at the periphery of the calibration carrier 208 and channel temperatures 504, 506, 508 maintained at the set of predetermined sample target temperatures 510, 512, 514, as a function of time. The temperatures 502 at the periphery of the calibration carrier 208 measured by the sensor 224 that maintain the temperatures 504-508 of the channels 214 at the predetermined set of target temperatures 510-514 are used to generate the temperature map 232.

Figure 6:
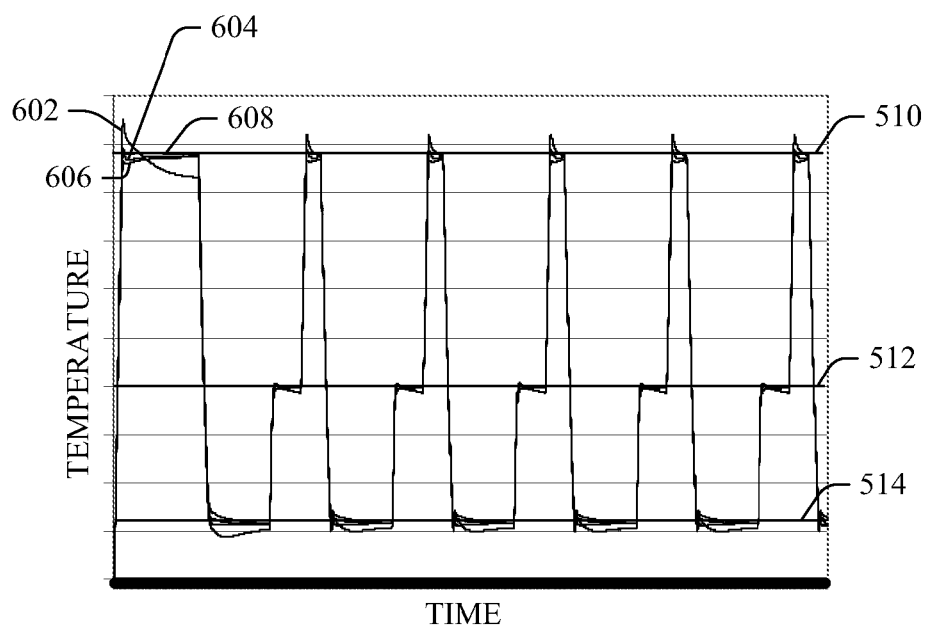
FIG. 6 illustrates an example graph showing the temperature at the periphery of a sample carrier and channel temperatures for the set of predetermined sample target temperatures using an approach in which the temperature of the thermal control device is controlled based on the set of sample target temperatures, temperatures measured at the periphery of the sample carrier, and a mapping between channel temperature and the temperature at the periphery of the sample carrier.

In sample processing mode, the thermal control system 224 controls the temperature of the TCD 222 and hence the temperature of the channels 210 in the PCR region 212 and the samples therein based on the predetermined set of target temperatures and corresponding timing 230, the temperature map 232, and the temperature at the periphery of the sample carrier 206, which is measured by the sensor 224. FIG. 6 illustrates an example graph showing temperatures 602 at the periphery of the sample carrier 206, sample temperatures 604, 606, 608, and the set of predetermined sample target temperatures 510, 512, 514, as a function of time, using an approach in which the TCD temperature is controlled based on the set of sample target temperatures, the temperature map, and temperatures measured at the periphery of the sample carrier by the sensor 224.

Note that in the examples of FIGS. 5 and 6, in order to maintain a substantially constant temperature for each of the target sample temperatures for each given time duration of each step (i.e., denaturing, annealing and extending), the temperature of the TCD 222 is varied non-linearly over the time duration. In another embodiment, the temperature of the TCD 222 may instead vary linearly and/or otherwise. In yet another embodiment, the temperature of the TCD 222 may instead be substantially constant.

It is to be understood that the geometry and/or spatial orientation of the components of FIGS. 2, 3 and 4 are provided for explanatory purposes and are not limiting. In addition, the target temperatures and corresponding timing 230 and/or the temperature map 232 can additionally or alternatively be included in medium other than that of the computer readable storage medium or memory 228 such as in transitory medium such as a carrier wave, a signal and/or other medium other than computer readable storage medium.

Figure 7:
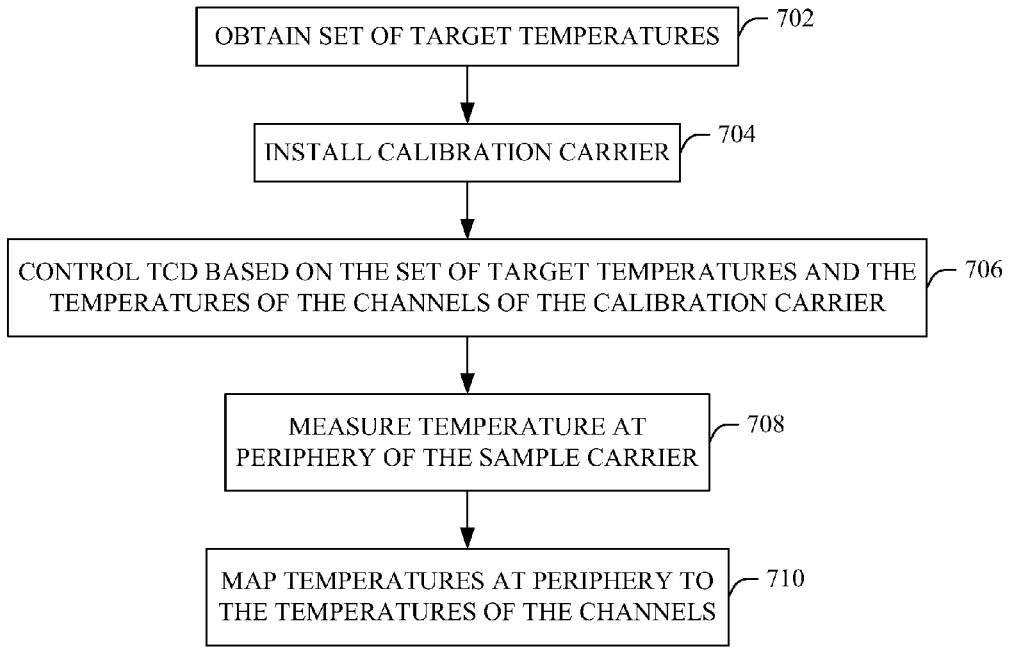
FIG. 7 illustrated an example approach for determining a temperature map, which maps channel temperature to the temperature at the periphery of the sample carrier.

FIG. 7 illustrates a non-limiting method for generating the temperature map 232.

It is to be appreciated that the ordering of the following acts is not limiting. As such, the acts can be otherwise ordered, including one or more of the acts being concurrent with one or more of the other acts. In addition, one or more of the acts may be omitted and/or one or more acts may be added.

At 702, a set of target sample temperatures is obtained for the sample processing apparatus 202. As discussed herein, the set of target temperatures may correspond to PCR temperatures and include the set of temperatures in the target temperature and corresponding timing 228.

At 704, the calibration carrier 208, which includes thermocouples in thermal communication with at least a sub-set of the channels of the calibration carrier, is installed in the carrier receiving region 204 of the sample processing apparatus 202, with the PCR region 216 in thermal communication with the TCD 222.

At 706, the TCD 222 is controlled so that the temperatures of the channels 214 in the PCR region 216 are cycled through the set of target sample temperatures. This may include taking a single measurement or multiple measurements for each of a plurality of the channels 214 via corresponding thermocouples 218, averaging the measurements across the channels to determine a representative temperature for the channels 214, and using the representative temperature as feedback to control the TCD 222.

At 708, concurrently with act 706, the sensor 224 is used to measure the temperature at the periphery of the calibration carrier 208.

At 710, the temperature map 232 is generated based on the temperatures at the periphery of the calibration carrier 208 and the representative temperature for the channels 214, for at least each of the temperatures in the set of target temperatures.

By way of example, for a denaturing temperature of 94±0.25° C., a channel temperature of 94° C. at time T1 may correspond to a TCD temperature of 98° C. as measured at the periphery of the calibration carrier 208, a channel temperature of 94° C. at time T2 may correspond to a TCD temperature of 95° C. as measured at the periphery of the calibration carrier 208, a channel temperature of 94° C. at time T3 may correspond to a TCD temperature of 93° C. as measured at the periphery of the calibration carrier 208, and a channel temperature of 94° C. at time T4 may correspond to a TCD temperature of 92° C. as measured at the periphery of the calibration carrier 208.

With this example, the temperature map 232 includes values that map a sample temperature of 94° C. to a TCD temperature of 98° C. at T1 as measured at the periphery of the sample carrier 206, a sample temperature of 94° C. to a TCD temperature of 95° C. at T2 as measured at the periphery of the sample carrier 206, a sample temperature of 94° C. to a TCD temperature of 93° C. at T3 as measured at the periphery of the sample carrier 206, and a sample temperature of 94° C. to a TCD temperature of 92° C. at T4 as measured at the periphery of the sample carrier 206.

It is to be understood that the above example is for explanatory purposes and is not limiting. For example, the mapping between channel temperature and TCD temperature may be different. In addition, the mapping may include more or less time points. Furthermore, the set of temperatures in the map may be used to determine other temperature mapping via interpolation, extrapolation, coefficient expansion, and/or otherwise. Moreover, a similar approach can be used to determine a mapping for the annealing and/or the extending steps of the replication process.

The temperature map 232 can be generated and/or updated before processing each set of samples, after processing a predetermined number of sets of samples, based on a predetermined time period, on demand, based on a calibration schedule, and/or other criteria.

Figure 8:
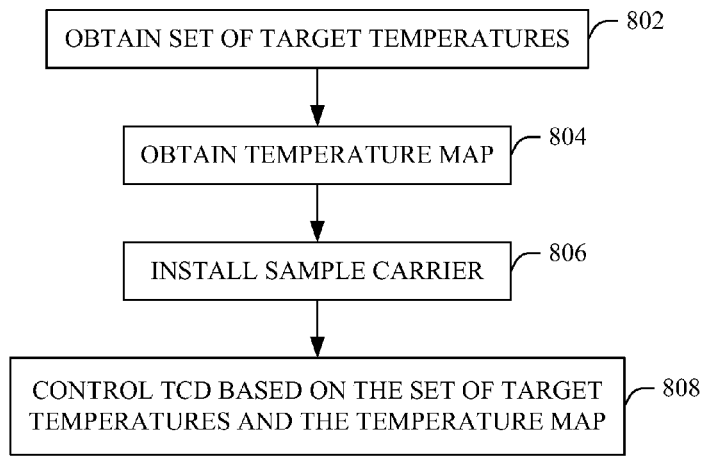
FIG. 8 illustrated an example approach for employing the temperature map to thermal cycle samples.

FIG. 8 illustrates a non-limiting method for employing the temperature map 232.

It is to be appreciated that the ordering of the following acts is not limiting. As such, the acts can be otherwise ordered, including one or more of the acts being concurrent with one or more other of the acts. In addition, one or more of the acts may be omitted and/or one or more acts may be added.

At 802, a set of target temperatures is obtained for the sample processing apparatus 202. As discussed herein, the set of target temperatures may correspond to PCR temperatures and include the set of temperatures in the target temperature and corresponding timing 228.

At 804, a temperature map 232 is obtained. As discussed herein, the temperature map 232 maps a set of target sample temperatures to TCD temperatures that thermal cycle the sample based on the set of target temperatures. FIG. 7 includes an example method for determining the temperature map 232.

At 806, the sample carrier 206 is installed in the carrier receiving region 204 of the sample processing apparatus 202 with the PCR region 212 in thermal communication with the TCD 222.

At 808, the TCD 222 is controlled based on the set of target temperatures of the target temperatures and corresponding timing 230 and the temperature map 232 to thermal cycle the sample(s) carried by the sample carrier 206, for example, in connection with PCR and DNA sample analysis based on the set of target temperatures of the target temperatures and corresponding timing 230.

By way of example, for a denaturing temperature of 94±0.25° C., where the temperature map maps a 94° C. sample temperature to a TCD temperature of 98° C. at T1, the thermal control system 226 controls the TCD 222 to produce a temperature of 98° C. at T1 as measured at the periphery of the sample carrier 206, where the temperature map maps a 94° C. sample temperature to a TCD temperature of 95° C. at T2, the thermal control system 226 controls the TCD 222 to produce a temperature of 95° C. at T2 as measured at the periphery of the sample carrier 206, etc.

Similar to FIG. 7, the above example is for explanatory purposes and is not limiting.

The above may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A method, comprising:
    obtaining, with a controller of a thermal control system, a target sample temperature, from a computer memory of the thermal control system that stores the target sample temperature, for a sample for a first sub-step, of a plurality of predetermined sub-steps, of a processing step, of a plurality of predetermined processing steps, to be performed on the sample, wherein the first sub-step of the processing step is one of a denaturing, an annealing or an extending of a replication of a polymerase chain reaction sub-step;
    obtaining, with the controller of the thermal control system, a temperature map, from the computer memory of the thermal control system that stores the temperature map, wherein the temperature map provides a mapping between the target sample temperature, as measured by a thermocouple in thermal communication with a channel of a calibration carrier with the target sample temperature applied to the channel, and a plurality of different temperatures for a thermal control device, wherein the plurality of different temperatures are different from each other and different from the target sample temperature and correspond to different time points, of a predetermined set of time points, of the first sub-step;
    identifying, with the controller of the thermal control system, for a first time point of the different time points for the first sub-step, a first temperature of the plurality of different temperatures using the mapping between the target sample temperature and the plurality of different temperatures and the first time point; and
    controlling, with the controller of the thermal control system, a temperature of the thermal control device at the first time point of the first sub-step to be the first temperature, wherein the thermal control device is in thermal communication with a channel of a sample carrier carrying the sample and controls a temperature of the sample.

2. The method of claim 1, further comprising:
    identifying, for a second time point of the different time points for the first sub-step, a second temperature of the plurality of different temperatures using the mapping between the target sample temperature and the plurality of different temperatures and the second time point; and
    controlling the temperature of the thermal control device at the second time point of the sub-step to be the second temperature.

3. The method of claim 2, wherein the controlling of the temperature at the second time point of the sub-step to be the second temperature includes changing the temperature non-linearly to change the temperature from the first temperature to the second temperature.

4. The method of claim 2, wherein the controlling of the temperature at the second time point of the sub-step to be the second temperature includes changing the temperature linearly to change the temperature from the first temperature to the second temperature.

5. The method of claim 2, further comprising:
    maintaining a temperature of the channel of the sample carrier carrying the sample at approximately a same temperature for the first and second time points of the sub-step by changing the temperature of the thermal control device from the first temperature at the first time point to the second temperature at the second time point.

6. The method of claim 2, further comprising:
    identifying, for at least one additional time point of the different time points, at least one additional temperature of the plurality of different temperatures using the mapping between the target sample temperature and the plurality of different temperatures and the at least one additional time point; and
    controlling the temperature of the thermal control device at the at least one additional time point of the sub-step to be the at least one additional temperature.

7. The method of claim 6, wherein the controlling of the temperature includes gradually changing the temperature from the second temperature to the at least one additional temperature.

8. The method of claim 6, further comprising:
    maintaining a temperature of the channel of the sample carrier carrying the sample at approximately a same temperature for the first, the second and the at least one additional time points of the sub-step by changing the temperature of the thermal control device from the first temperature at the first time point to the second temperature at the second time point to the at least one additional temperature at the at least one additional time point.

9. The method of claim 8, wherein maintaining the temperature of the channel maintains an approximately constant temperature of the sample.

10. The method of claim 9, wherein the approximately constant temperature is a temperature from a group consisting of: 94±0.25° C.; 56±0.25° C., and 70±0.25° C.

11. The method of claim 1, wherein the processing step is a DNA sequencing step.

12. The method of claim 1, wherein for each of the denaturing, the annealing and the extending of replication, the temperature of the sample is approximately constant.

13. The method of claim 1, further comprising:
    controlling, with the controller of the thermal control system, the temperature of the thermal control device to set a temperature of a channel of a calibration carrier at the target sample temperature;
    measuring, with the thermocouple in thermal communication with the channel of the calibration carrier, a temperature of the calibration carrier concurrently with controlling the temperature of the channel of the thermal control device which results in the temperature of the channel of the calibration carrier being at the target sample temperature; and
    determining, with the controller of the thermal control system, the mapping between the target sample temperature and a first temperature of the plurality of different temperatures based on the target sample temperature and the measured temperature.

14. The method of claim 13, wherein the temperature of the calibration carrier is a temperature at a periphery of the calibration carrier, and temperature at the periphery of the calibration carrier is different from the temperature of the channel.

15. The method of claim 1, further comprising:
obtaining at least one additional target sample temperature, wherein the temperature map provides at least one additional mapping between the at least one additional target sample temperature and at least one additional set of temperatures of the thermal control device for at least one additional sub-step of the processing step;
identifying, for a time point of the at least one additional sub-step, a temperature of the at least one additional set of temperatures using the at least one additional mapping between the at least one additional target sample temperature and the at least one additional set of temperatures and the time point of the at least one additional sub-set; and
controlling the temperature of the thermal control device at the time point of the at least one additional sub-set at the at least one additional set of temperatures.

16. The method of claim 14, further comprising:
controlling the temperature of the thermal control device to set a temperature of a channel of a calibration carrier at the target sample temperature;
measuring a temperature at a periphery of the calibration carrier concurrently with controlling the temperature of the thermal control device to set the temperature of the channel of the calibration carrier at the target sample temperature; and
determining the mapping between the target sample temperature and a first temperature of the plurality of different temperatures based on the target sample temperature and the measured temperature.

17. The method of claim 16, further comprising:
controlling the temperature of the thermal control device to set the temperature of the channel of the calibration carrier at the at least one additional target sample temperature;
measuring the temperature at the periphery of the calibration carrier concurrently with controlling the temperature of the thermal control device to set the temperature of the channel of the calibration carrier at the at least one additional target sample temperature; and
determining the mapping between the at least one additional target sample temperature and a second temperature of the plurality of different temperatures based on the at least one additional target sample temperature and the measured temperature.

18. The method of claim 17, wherein the target sample temperature and the at least one additional target sample temperature are from a group consisting of: 94±0.25° C.; 56±0.25° C., and 70±0.25° C.

19. The method of claim 11, wherein the thermal control device is a thermoelectric cooler.

20. A method, comprising:
obtaining, with a controller of a thermal control system, a target sample temperature, from a computer memory of the thermal control system that stores the target sample temperature, for a sample for a first sub-step, of a plurality of predetermined sub-steps, of a processing step, of a plurality of predetermined processing steps, to be performed on the sample;
obtaining, with the controller of the thermal control system, a temperature map, from the computer memory of the thermal control system that stores the temperature map, wherein the temperature map provides a mapping between the target sample temperature, as measured by a thermocouple in thermal communication with a channel of a calibration carrier with the target sample temperature applied to the channel, and a plurality of different temperatures for a thermal control device, wherein the plurality of different temperatures are different from each other and different from the target sample temperature and correspond to different time points, of a predetermined set of time points, of the first sub-step;
identifying, with the controller of the thermal control system, for a first time point of the different time points for the first sub-step, a first temperature of the plurality of different temperatures using the mapping between the target sample temperature and the plurality of different temperatures and the first time point; and
controlling, with the controller of the thermal control system, a temperature of the thermal control device at the first time point of the first sub-step to be the first temperature, wherein the thermal control device is in thermal communication with a channel of a sample carrier carrying the sample and controls a temperature of the sample, and wherein the thermal control device is a thermoelectric cooler.

21. An apparatus, comprising:
a controller of a thermal control system configured to:
obtain a target sample temperature, from a computer memory of the thermal control system that stores the target sample temperature, for a sample for a first sub-step, of a plurality of predetermined sub-steps, of a processing step, of a plurality of predetermined processing steps, to be performed on the sample, wherein the first sub-step of the processing step is one of a denaturing, an annealing or an extending of a replication of a polymerase chain reaction sub-step;
obtain a temperature map, from the computer memory of the thermal control system that stores the temperature map, wherein the temperature map provides a mapping between the target sample temperature, as measured by a thermocouple in thermal communication with a channel of a calibration carrier with the target sample temperature applied to the channel, and a plurality of different temperatures for a thermal control device, wherein the plurality of different temperatures are different from each other and different from the target sample temperature and correspond to different time points, of a predetermined set of time points, of the first sub-step;
identify, for a first time point of the different time points for the first sub-step, a first temperature of the plurality of different temperatures using the mapping between the target sample temperature and the plurality of different temperatures and the first time point; and
control a temperature of the thermal control device at the first time point of the first sub-step to be the first temperature, wherein the thermal control device is in thermal communication with a channel of a sample carrier carrying the sample and controls a temperature of the sample.

22. An apparatus, comprising:
a controller of a thermal control system configured to:
obtain a target sample temperature, from a computer memory of the thermal control system that stores the target sample temperature, for a sample for a first sub-step, of a plurality of predetermined sub-steps, of a processing step, of a plurality of predetermined processing steps, to be performed on the sample;

obtain a temperature map, from the computer memory of the thermal control system that stores the temperature map, wherein the temperature map provides a mapping between the target sample temperature, as measured by a thermocouple in thermal communication with a channel of a calibration carrier with the target sample temperature applied to the channel, and a plurality of different temperatures for a thermal control device, wherein the plurality of different temperatures are different from each other and different from the target sample temperature and correspond to different time points, of a predetermined set of time points, of the first sub-step;

identify, for a first time point of the different time points for the first sub-step, a first temperature of the plurality of different temperatures using the mapping between the target sample temperature and the plurality of different temperatures and the first time point; and control a temperature of the thermal control device at the first time point of the first sub-step to be the first temperature, wherein the thermal control device is in thermal communication with a channel of a sample carrier carrying the sample and controls a temperature of the sample, and wherein the thermal control device is a thermoelectric cooler.

* * * * *